(12) United States Patent
Azizian

(10) Patent No.: US 12,011,236 B2
(45) Date of Patent: Jun. 18, 2024

(54) SYSTEMS AND METHODS FOR RENDERING ALERTS IN A DISPLAY OF A TELEOPERATIONAL SYSTEM

(71) Applicant: INTUITIVE SURGICAL OPERATIONS, INC., Sunnyvale, CA (US)

(72) Inventor: Mahdi Azizian, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 637 days.

(21) Appl. No.: 16/637,461

(22) PCT Filed: Aug. 6, 2018

(86) PCT No.: PCT/US2018/045366
§ 371 (c)(1),
(2) Date: Feb. 7, 2020

(87) PCT Pub. No.: WO2019/032450
PCT Pub. Date: Feb. 14, 2019

(65) Prior Publication Data
US 2020/0246084 A1    Aug. 6, 2020

Related U.S. Application Data

(60) Provisional application No. 62/542,457, filed on Aug. 8, 2017.

(51) Int. Cl.
*A61B 34/00* (2016.01)
*A61B 34/37* (2016.01)
*A61B 90/00* (2016.01)

(52) U.S. Cl.
CPC .............. *A61B 34/25* (2016.02); *A61B 34/37* (2016.02); *A61B 34/70* (2016.02); *A61B 34/76* (2016.02);
(Continued)

(58) Field of Classification Search
None
See application file for complete search history.

(56) References Cited

U.S. PATENT DOCUMENTS

| 4,219,999 A | * | 9/1980 | Ichikawa | ................. G04C 3/14 368/80 |
| 2004/0024311 A1 | * | 2/2004 | Quaid, III | .............. A61B 90/36 600/428 |

(Continued)

FOREIGN PATENT DOCUMENTS

| KR | 20150000279 A | 1/2015 |
| KR | 20150093787 A | 8/2015 |

(Continued)

OTHER PUBLICATIONS

International Search Report and Written Opinion for Application No. PCT/US2018/045366, dated Nov. 27, 2018, 9 pages.

(Continued)

*Primary Examiner* — David H Chu
(74) *Attorney, Agent, or Firm* — Haynes & Boone, LLP.

(57) ABSTRACT

A method comprises displaying a surgical environment image. The surgical environment image includes a field of view image obtained by a first imaging system. The method also includes receiving alert information and providing an alert indication, based upon the alert information, within the surgical environment image by altering a portion of the surgical environment image.

4 Claims, 7 Drawing Sheets

(52) U.S. Cl.
CPC ........ *A61B 90/37* (2016.02); *A61B 2034/252* (2016.02); *A61B 2090/365* (2016.02); *A61B 2090/371* (2016.02); *A61B 2090/3762* (2016.02)

(56) References Cited

U.S. PATENT DOCUMENTS

| | | | | |
|---|---|---|---|---|
| 2005/0267354 | A1* | 12/2005 | Marquart | A61B 90/36 600/407 |
| 2007/0016016 | A1* | 1/2007 | Haras | A61B 6/507 600/407 |
| 2008/0058608 | A1* | 3/2008 | Garibaldi | A61B 6/02 600/300 |
| 2008/0176550 | A1* | 7/2008 | Skinner | H04W 8/245 455/419 |
| 2009/0192524 | A1* | 7/2009 | Itkowitz | A61B 34/30 606/130 |
| 2009/0262144 | A1* | 10/2009 | Kawagishi | G05B 19/409 345/661 |
| 2011/0158494 | A1* | 6/2011 | Bar-Shalev | A61B 6/5241 382/131 |
| 2011/0224574 | A1* | 9/2011 | Sadler | G01N 33/5091 600/562 |
| 2011/0306986 | A1* | 12/2011 | Lee | A61B 34/37 606/130 |
| 2014/0055489 | A1* | 2/2014 | Itkowitz | G06T 11/40 345/633 |
| 2014/0343416 | A1* | 11/2014 | Panescu | A61B 34/30 600/431 |
| 2014/0350404 | A1* | 11/2014 | Rajguru | A61B 8/5223 600/443 |
| 2015/0095790 | A1* | 4/2015 | Yoshida | G08C 17/02 715/740 |
| 2015/0097685 | A1* | 4/2015 | Sloo | G08B 21/14 340/632 |
| 2015/0359418 | A1* | 12/2015 | Feussner | G02B 23/2461 600/111 |
| 2016/0008078 | A1 | 1/2016 | Azizian et al. | |
| 2016/0191887 | A1* | 6/2016 | Casas | H04N 13/111 348/47 |
| 2016/0343241 | A1* | 11/2016 | Rossi | G08B 29/126 |
| 2017/0281282 | A1* | 10/2017 | Noonan | A61B 17/1764 |
| 2017/0284902 | A1* | 10/2017 | Nolan | H04W 4/70 |
| 2017/0329428 | A1* | 11/2017 | Seong | G06F 1/1652 |
| 2017/0333137 | A1* | 11/2017 | Roessler | A61B 17/1703 |
| 2017/0358083 | A1* | 12/2017 | Piron | A61B 90/361 |
| 2018/0263704 | A1* | 9/2018 | Lang | A61B 17/1775 |
| 2019/0110181 | A1* | 4/2019 | Kavantsaari | G08B 25/001 |
| 2020/0405433 | A1* | 12/2020 | Sela | G06T 7/33 |

FOREIGN PATENT DOCUMENTS

| | | |
|---|---|---|
| WO | WO-2015142798 A1 | 9/2015 |
| WO | WO-2015142956 A1 | 9/2015 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2018/045366, dated Feb. 20, 2020, 8 pages.

* cited by examiner

SYSTEMS AND METHODS FOR RENDERING ALERTS IN A DISPLAY OF A TELEOPERATIONAL SYSTEM

CROSS-REFERENCE TO RELATED APPLICATIONS

This patent application is the U.S. national phase of International Application No. PCT/US2018/045366, filed Aug. 6, 2018, which designated the U.S. and claims priority to and the benefit of U.S. Provisional Application 62/542,457 filed Aug. 8, 2017, all of which are incorporated by reference herein in their entirety.

FIELD

The present disclosure is directed to systems and methods for performing a teleoperational medical procedure and more particularly to systems and methods for displaying alerts in a surgical environment image displayed by a teleoperational system.

BACKGROUND

Minimally invasive medical techniques are intended to reduce the amount of tissue that is damaged during invasive medical procedures, thereby reducing blood loss, patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted. In existing teleoperational medical systems, information may be displayed to a user in message windows outside of the surgical environment image along the border of the display or in discrete indicator overlays to an endoscopic image of a surgical environment. Systems and methods are needed to provide alerts within the surgical environment image by visually deforming regions of the image. Thus, the alerts may be co-located with anatomic structures or instruments associated with the alerts.

SUMMARY

The embodiments of the invention are summarized by the claims that follow below.

In one embodiment, a method comprises displaying a surgical environment image. The surgical environment image includes a field of view image obtained by a first imaging system. The method also includes receiving alert information and providing an alert indication, based upon the alert information, within the surgical environment image by altering a portion of the surgical environment image.

In another embodiment, a system comprises a teleoperational assembly including a plurality of manipulators configured for teleoperation by an operator control system. A first manipulator of the plurality of manipulators is configured to control movement of a first medical instrument in a surgical environment and a second manipulator of the plurality of manipulators is configured to control movement of a first imaging system. The system also comprises a processing unit including one or more processors. The processing unit is configured to display a surgical environment image. The environment image includes a field of view image obtained by the first imaging system. The processing unit is also configured to receive alert information and provide an alert indication, based upon the alert information, within the surgical environment image by altering a portion of the surgical environment image.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
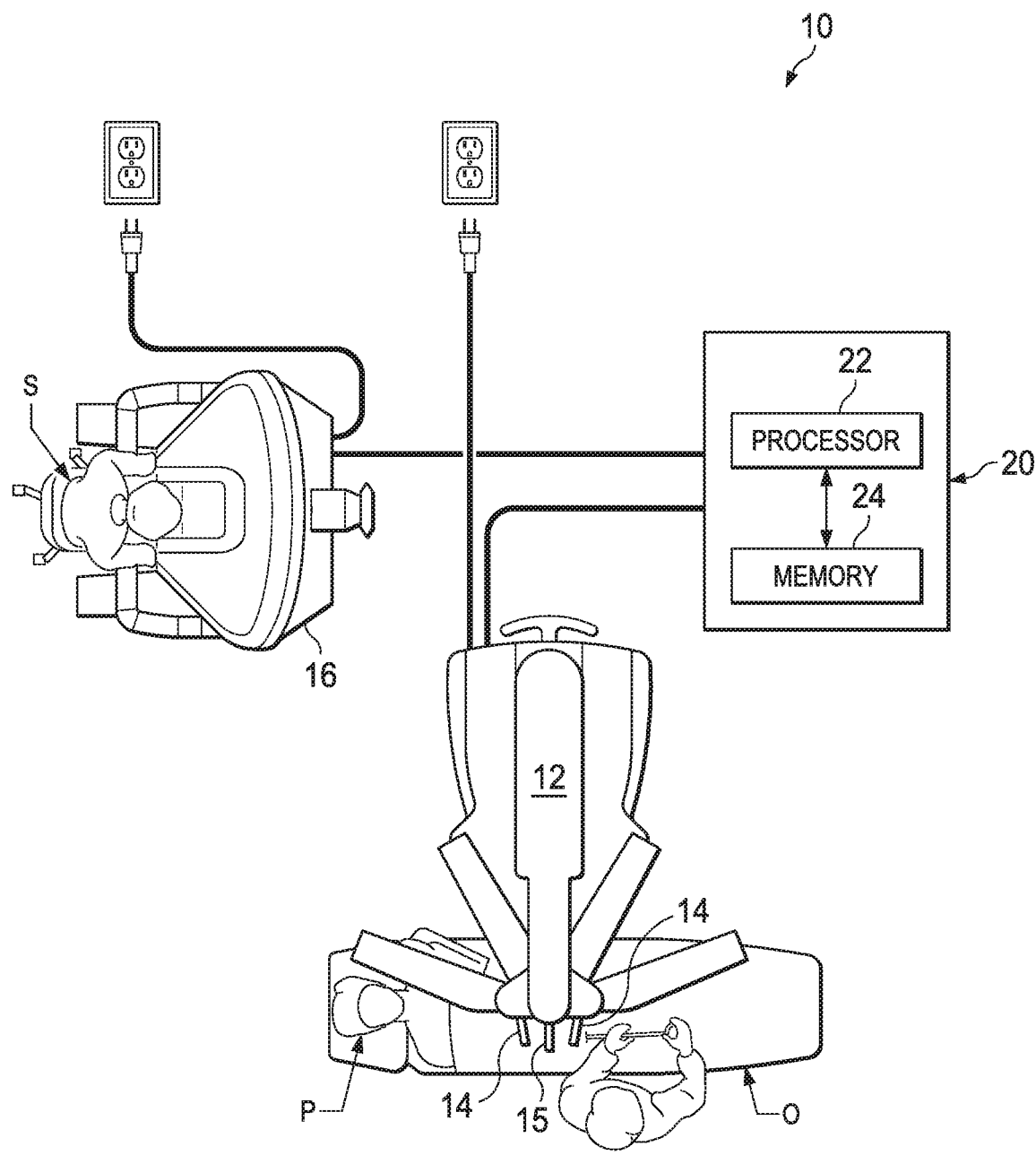
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom).

Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 mounted to or near an operating table O on which a patient P is positioned. The teleoperational assembly 12 may be referred to as a patient side cart. A medical instrument system 14 and an endoscopic imaging system 15 are operably coupled to the teleoperational assembly 12. An operator input system 16 allows a surgeon or other type of clinician S to view images of or representing the surgical site and to control the operation of the medical instrument system 14 and/or the endoscopic imaging system 15.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaw end effectors, applying an electrical potential to an electrode, delivering a medicinal treatment, and the like).

The teleoperational assembly 12 supports and manipulates the medical instrument system 14 while the surgeon S views the surgical site through the console 16. An image of the surgical site can be obtained by the endoscopic imaging system 15, such as a stereoscopic endoscope, which can be manipulated by the teleoperational assembly 12 to orient the endoscope 15. The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator. The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Instruments 14 may include end effectors having a single working member such as a scalpel, a blunt blade, an optical fiber, or an electrode. Other end effectors may include, for example, forceps, graspers, scissors, or clip appliers.

The teleoperational medical system 10 also includes a control system 20. The control system 20 includes at least one memory 24 and at least one processor 22, and typically a plurality of processors, for effecting control between the medical instrument system 14, the operator input system 16, and other auxiliary systems 26 which may include, for example, imaging systems, audio systems, fluid delivery systems, display systems, illumination systems, steering control systems, irrigation systems, and/or suction systems. The control system 20 can be used to process the images of the surgical environment from the imaging system 15 for subsequent display to the surgeon S through the surgeon's console 16. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 may support wireless communication protocols such as IEEE 802.15 (Bluetooth, ZigBee and the like), IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The control system 20 can be coupled with the endoscope 15 and can include a processor to process captured images for subsequent display, such as to a surgeon on the surgeon's console, or on another suitable display located locally and/or remotely. For example, where a stereoscopic endoscope is used, the control system 20 can process the captured images to present the surgeon with coordinated stereo images of the surgical site. Such coordination can include alignment between the opposing images and can include adjusting the stereo working distance of the stereoscopic endoscope.

In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 1B:
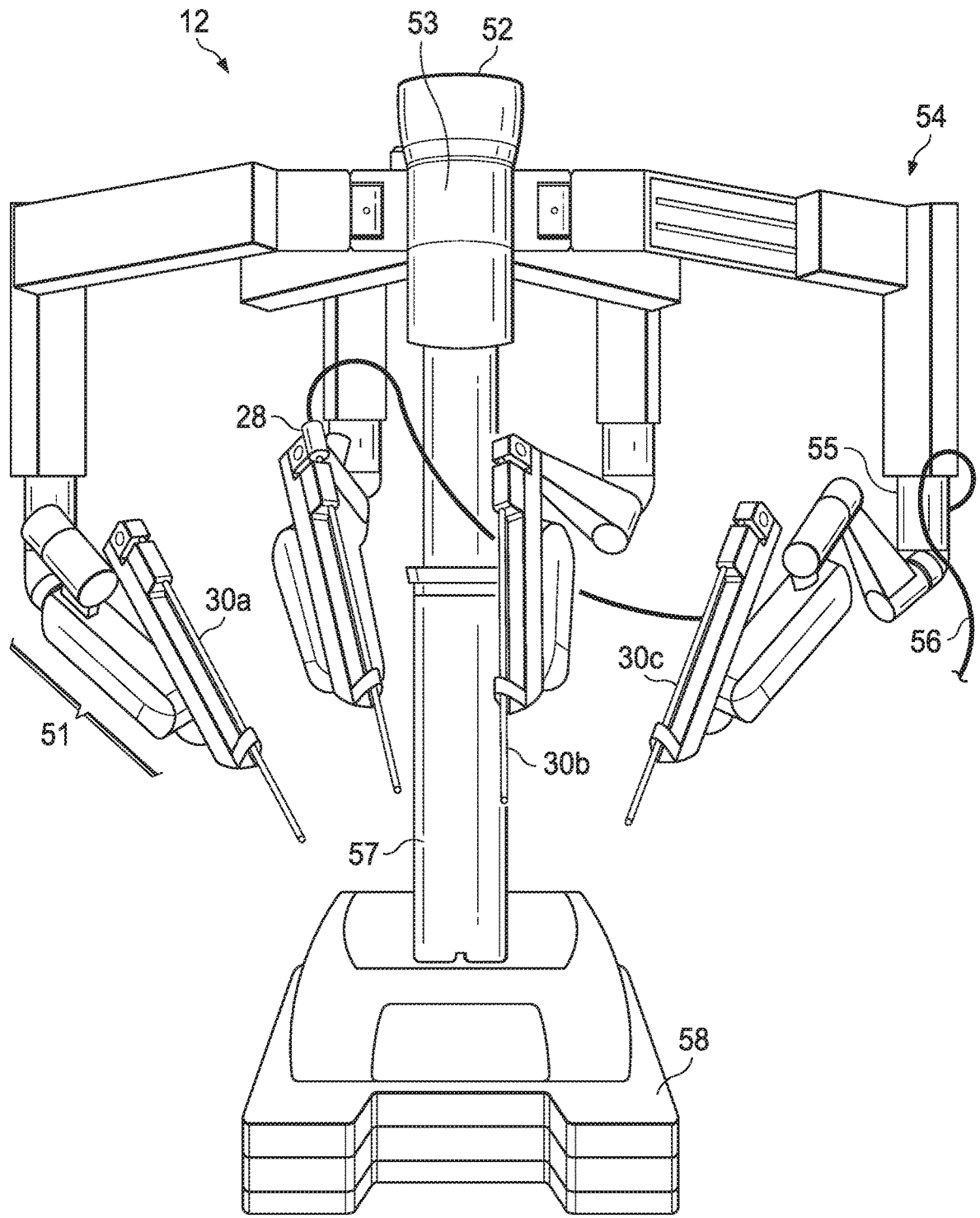
FIG. 1B is a perspective view of a teleoperational manipulator, according to one example of principles described herein.

FIG. 1B is a perspective view of one embodiment of a teleoperational assembly 12 which may be referred to as a patient side cart. The patient side cart 12 shown provides for the manipulation of three surgical tools 30a, 30b, 30c (e.g., instrument systems 14) and an imaging device 28 (e.g., endoscopic imaging system 15), such as a stereoscopic endoscope used for the capture of images of the site of the procedure. The imaging device may transmit signals over a cable 56 to the control system 20. Manipulation is provided by teleoperative mechanisms having a number of joints. The imaging device 28 and the surgical tools 30a-c can be positioned and manipulated through incisions in the patient so that a kinematic remote center is maintained at the incision to minimize the size of the incision. Images of the surgical environment within the patient anatomy can include images of the distal ends of the surgical tools 30a-c when they are positioned within the field-of-view of the imaging device 28.

The patient side cart 22 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The patient side cart 22 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument 26. The manipulator arms 51 may be teleoperatable. In some examples, the arms 54 connecting to the orienting platform are not teleoperatable. Rather, such arms 54 are positioned as desired before the surgeon 18 begins operation with the teleoperative components.

Endoscopic imaging systems (e.g., systems 15, 28) may be provided in a variety of configurations including rigid or flexible endoscopes. Rigid endoscopes may include a rigid tube housing a relay lens system for transmitting an image from a distal end to a proximal end of the endoscope. Flexible endoscopes may transmit images using one or more flexible optical fibers. Digital image based endoscopes have a "chip on the tip" design in which a distal digital sensor such as a one or more charge-coupled device (CCD) or a complementary metal oxide semiconductor (CMOS) device capture image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle and shaft all rigidly coupled and hermetically sealed.

Figure 1C:
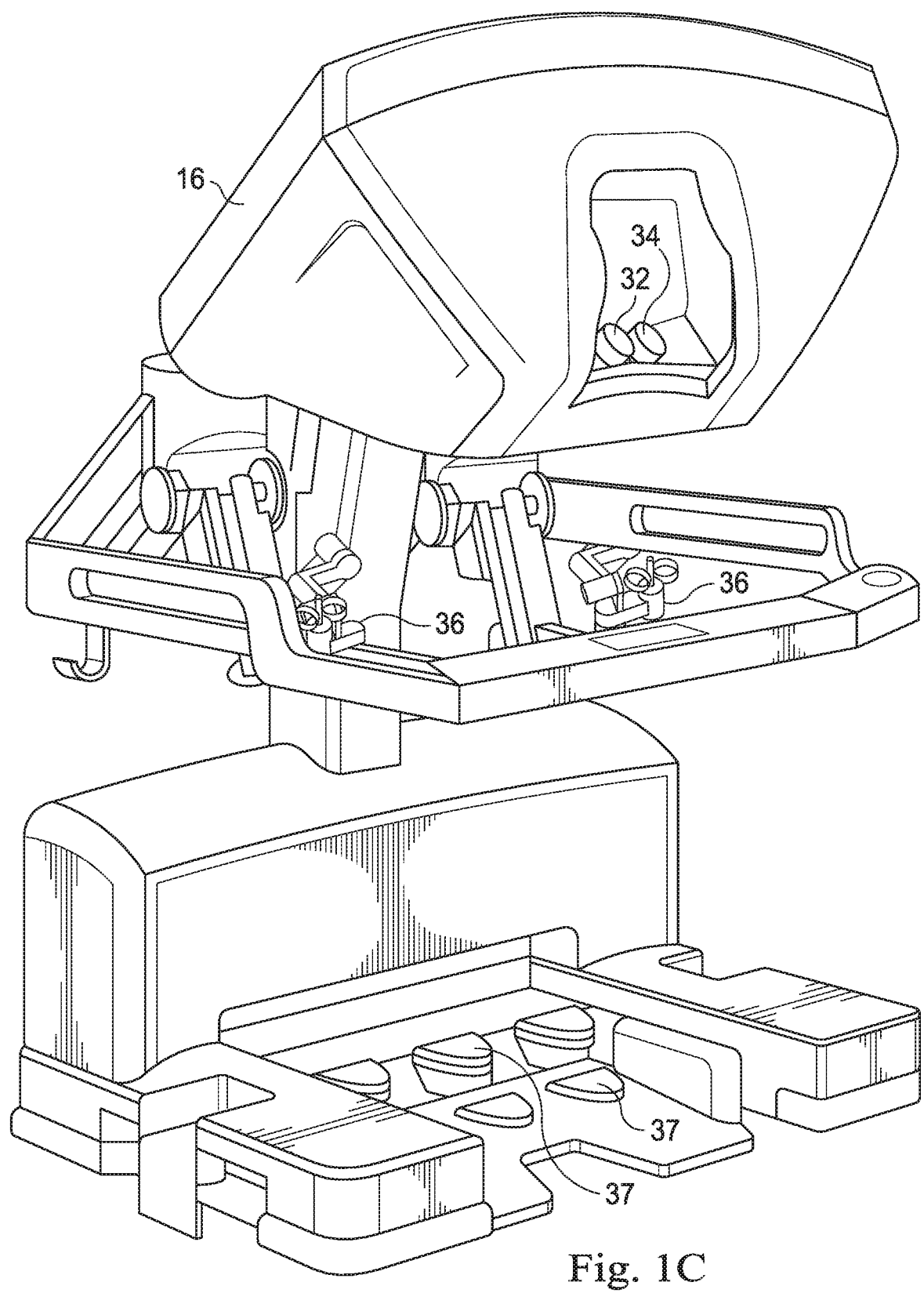
FIG. 1C is a perspective view of a surgeon's control console for a teleoperational medical system, in accordance with many embodiments.

FIG. 1C is a perspective view of the surgeon's console 16. The surgeon's console 16 includes a left eye display 32 and a right eye display 34 for presenting the surgeon S with a coordinated stereo view of the surgical environment that enables depth perception. The displayed image of the surgical environment may be obtained from an imaging system such as the endoscopic imaging system. Additionally or alternatively, the displayed image of the surgical environment may include images from anatomic models created from pre-operative or intra-operative image data sets. Pre-operative or intraoperative image data sets of the patient anatomy may be obtained using imaging technology such as computerized tomography (CT), magnetic resonance imaging (MRI), single-photon emission computed tomography (SPECT), positron emission tomography (PET), X-ray fluoroscopy, ultrasound imaging, photoacoustic imaging, optical coherence tomography (OCT), thermal imaging, impedance imaging or the like. Software alone or in combination with manual input is used to convert the recorded images into segmented two dimensional or three dimensional composite models representing a partial or an entire anatomical organ or anatomical region. An image data set is associated with the composite representation. The images used to generate the composite representation may be recorded preoperatively or intra-operatively during a clinical procedure. The pre-operative or intra-operative image data may be presented as two-dimensional, three-dimensional, or four-dimensional (including e.g., time based or velocity based information) images or as images from models created from the pre-operative or intra-operative image data sets. Images from different imaging modalities may be displayed one at a time (e.g., the surgeon may toggle through the different modality images), may be displayed in parallel (e.g., in multiple windows of a composite display) or one may be overlaid or superimposed on the other.

The console 16 further includes one or more input control devices 36, which in turn cause the teleoperational assembly 12 to manipulate one or more instruments or the endoscopic imaging system. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36. Input control devices 37 are foot pedals that receive input from a user's foot.

During a teleoperational procedure, various alerts may be provided to the surgeon including alerts about registration errors between the patient anatomy and the endoscopic image or registration errors between the endoscopic image and a pre- or intra-operative patient model. Alternatively, the alerts may relate to information from a proctor at an operator input system, information related to medical instruments or the teleoperational manipulators, or information about the surgical procedure. Alerts may be displayed by modifying a portion of the surgeon's surgical environment image that relates to the anatomical structures or medical instruments involved in the alert.

Figure 2:
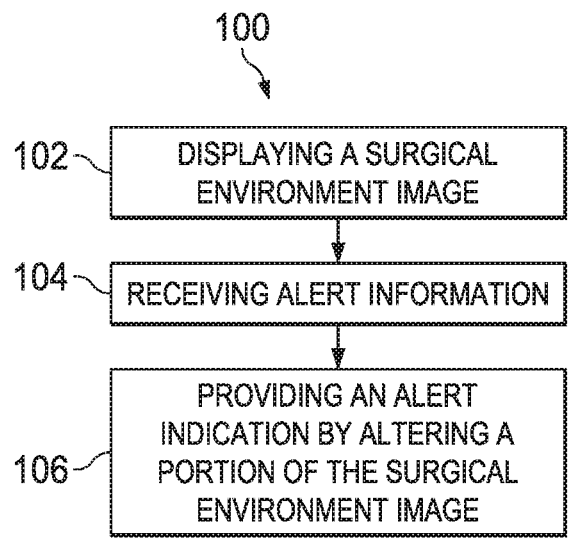
FIG. 2 illustrates a method of providing an alert within a surgical environment image.

FIG. 2 is a flowchart illustrating a method 100 of providing an alert within a surgical environment image. The method 100 is illustrated in FIG. 2 as a set of operations or processes. Not all of the illustrated processes may be performed in all embodiments of method 100. Additionally, one or more processes that are not expressly illustrated in FIG. 2 may be included before, after, in between, or as part of the illustrated processes. In some embodiments, one or more of the processes of method 100 may be implemented, at least in part, in the form of executable code stored on non-transitory, tangible, machine-readable media that when run by one or more processors (e.g., the processors of control system 20) may cause the one or more processors to perform one or more of the processes.

At a process 102, a surgical environment image is displayed, for example on a display of the surgeon's console 16. The surgical environment image may be a two or three dimensional image of a surgical field of view obtained by an endoscopic system (e.g., system 15, 28). As described below for method 150, in some embodiments, the surgical environment image may also include an overlaid and registered anatomic model image obtained by a pre-operative or intra-operative external, non-invasive imaging system such at a CT imaging system.

At a process 104, alert information from one or more components of the teleoperational system 10 is received. The alert information may be, for example, a warning, status information, error information, instructions from a mentor or proctor at another surgical console, or information about a next step in a surgical procedure.

Figure 4:
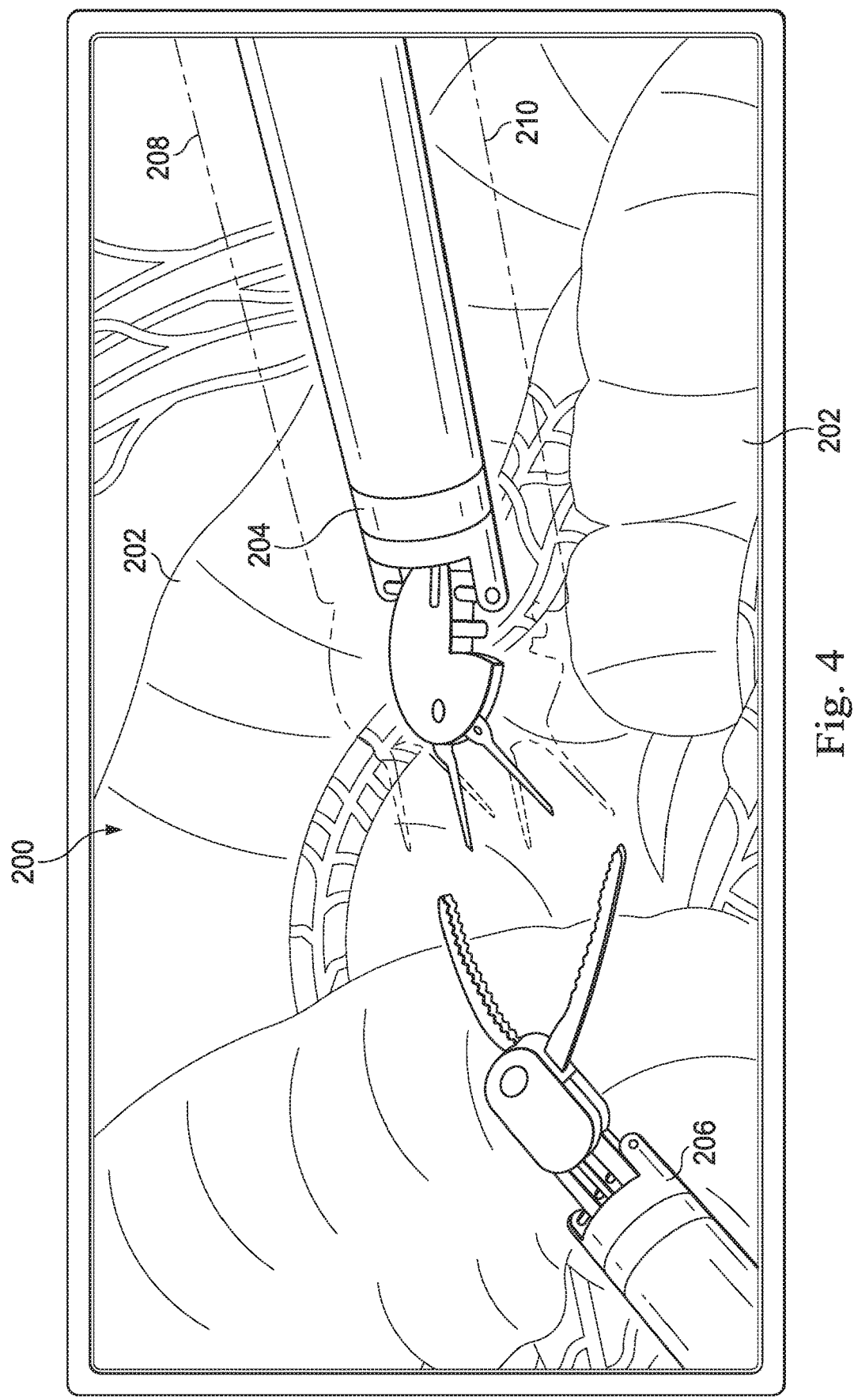
FIG. 4 is a display of a surgical environment image including an alert indication according to one example.
Figure 5:
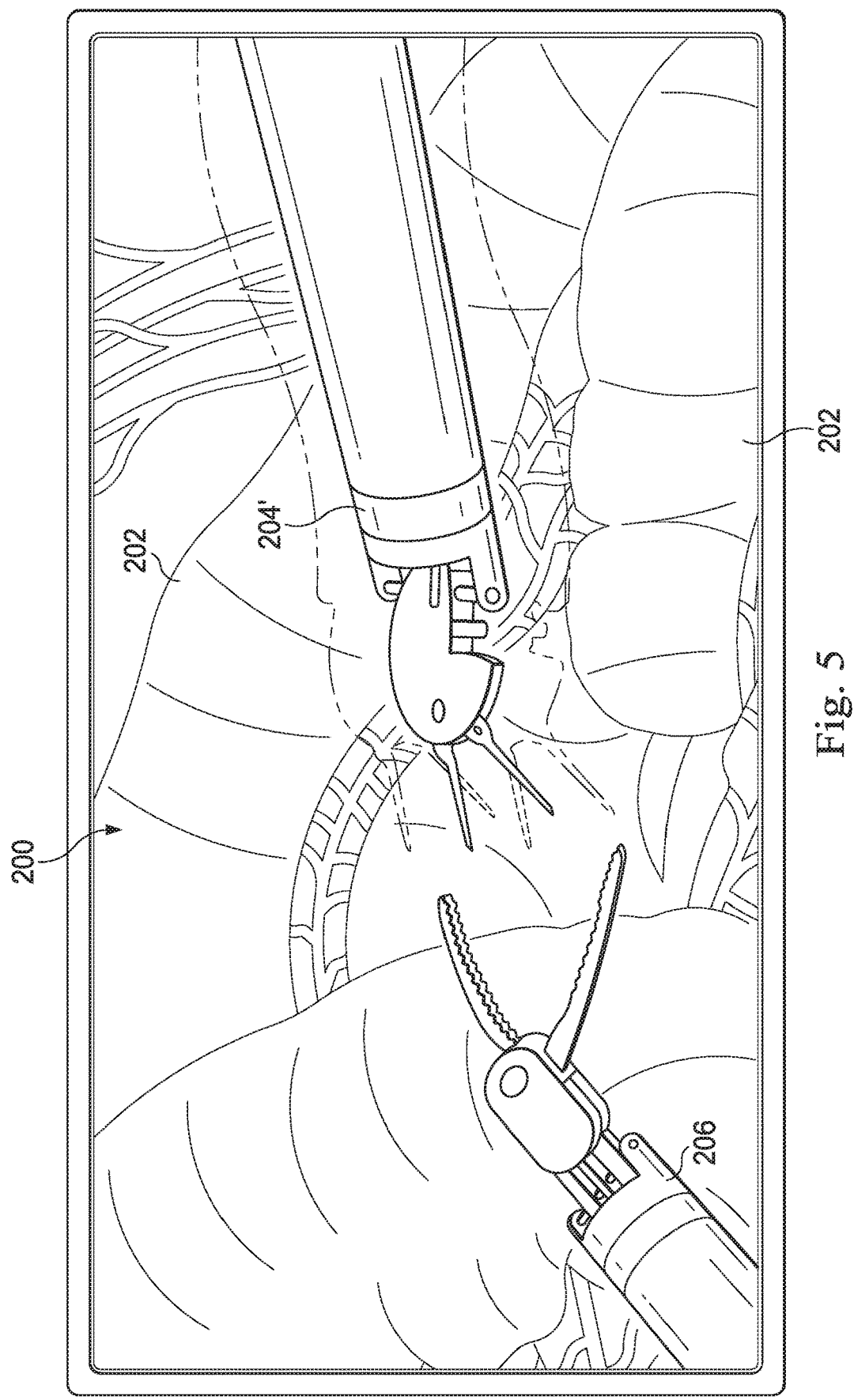
FIG. 5 is a display of a surgical environment image including an alert indication according to another example.

At a process 106, the alert information is processed to provide an alert indication within the surgical environment image by altering at least a portion of the surgical environment image. FIG. 4 illustrates one example of a displayed surgical environment image 200 including an alert indication. In this example, the image 200 is an endoscopic field of view image depicting tissue 202 in the surgical site, a distal end of a medical instrument 204, and a distal end of a medical instrument 206. The medical instruments 204, 206 may be the same or similar to instruments 15 and tools 30. In this example, the alert information may be, for example, that instrument 204, or the manipulator to which it is attached, has collided with another instrument or manipulator or has otherwise reached a motion boundary and is not able to respond as commanded by the surgeon at the console 16. The control system 20 processes that alert information and provides an alert indication in the form of a modulated image of the instrument 204. In this example, the modulated image is the sub-portion of the endoscope image 200 including the instrument 204. The endoscope image data stream may be routed through the processing unit of the control system 20 to modify or animate specific portions of the image. More specifically, a three dimensional point cloud of image pixels forming the instrument 204 in the field of view image 200 are identified. The point cloud is geometrically modulated (e.g., by moving some or all other points linearly in the image plane or in and out of the image plane of the stereoscopic image) to create an animated image of the instrument 204. For example, the animation may create the appearance that the image of the instrument 204 is vibrating, pulsating, or undulating in a wave or ripple form. Alternatively, the subportion of the image 200 including the instrument 204 may be altered by applying a blur or fade effect to the image of the instrument 204 to create the alert indication. In FIG. 4, instrument 204 is animated to create the appearance that the instrument is moving with a virtual vibration motion. The animated instrument 204 is modulated between an upper displacement limit 208 and a lower displacement limit 210. FIG. 5 illustrates the surgical environment image 200 with an image of the instrument 204' modulated to create an animated wave motion. As the images of the instrument 204, 204' are modulated, the remaining portions of the surgical environment image 200, including the images of other instruments, remain unaltered, thus appearing still or unmodulated. Alternatively, the disparity between left and right images around the area of instrument 204 may be altered to indicate out of plane depth changes of the instrument.

In various alternative examples, the alert indication can be used to indicate instrument function or malfunction. For example, an alert indication may be used to indicate that energy has been actuated for a cauterization instrument. For example, an alert indication may be used to indicate that a stapler has completed a staple firing operation. In various alternative examples, the alert indication can be used to provide instruction from a proctor or tele-mentor at another surgical console. For example, the alert indication may be used by the proctor to indicate that the surgeon should next move the instrument 204 or to indicate how the surgeon should operate the instrument 204. For example, the animation may modify the image to show the jaws of the instrument virtually closing, thus indicating to the user to take action at the surgeon's console to cause the jaws to actually close. In various alternative examples, the alert indication may be a local change in image parameters such as pixel brightness, color, or gray-scale. In various alternative examples, the alert indication may animate the shaft of the instrument 204 but not the end effector or distal tip to avoid a compensatory reaction from the surgeon. In an alternative example, a voluntary action may be required upon display of an alert, in order to get back the master-slave control of the instrument to avoid compensatory reaction from the surgeon. In an alternative example, visual alert indication may be accompanied by a haptic alert, such as a vibration, on the master manipulators 36. In various alternative examples, the alert indication may animate the distal tip/end effector of the instrument 204 but not the shaft to indicate actuation of the end effector. In various alternative examples, the alert indication may animate the anatomic tissue 202 to show the surgeon a suggested next task or action in a surgical procedure. For example, the portion of the image 200 including a section of tissue 202 may be modified to provide a virtual cut-away view of the tissue and may be animated to show the movement of the cut-away tissue. This may serve as an indication to the surgeon to perform the tissue cut as a next step in the surgical procedure. Similarly, a section of tissue 202 may be modified (e.g., animated to vibrate or undulate) to indicate to the surgeon which portion of the anatomy to select. For example the image of a blood vessel may be modulated to indicate to the surgeon which of a plurality of blood vessels to select for cauterization.

The alert indication may provide information about the proximity of a surgical instrument tip to a critical structure (e.g., an artery, vein, tumor) in an anatomic model of a patient. The alert indication may also provide information about the proximity of a surgical instrument tip to a preoperative surgical plan such as a trajectory or surface specifying a no-fly zone or a suggested cut-plane on the anatomic model of the patient.

Figure 3:
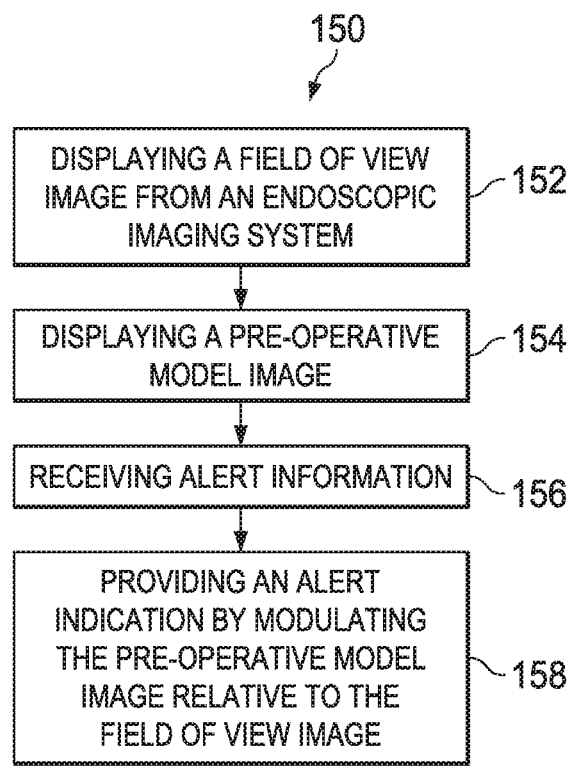
FIG. 3 illustrates another method of providing an alert within a surgical environment image.

FIG. 3 is a flowchart illustrating another method 150 of providing an alert within a surgical environment image to indicate a registration error between an anatomic model image and an endoscopic image. The method 150 is illustrated in FIG. 3 as a set of operations or processes. Not all of the illustrated processes may be performed in all embodiments of method 150. Additionally, one or more processes that are not expressly illustrated in FIG. 3 may be included before, after, in between, or as part of the illustrated processes. In some embodiments, one or more of the processes of method 150 may be implemented, at least in part, in the form of executable code stored on non-transitory, tangible, machine-readable media that when run by one or more processors (e.g., the processors of control system 20) may cause the one or more processors to perform one or more of the processes.

Figure 6:
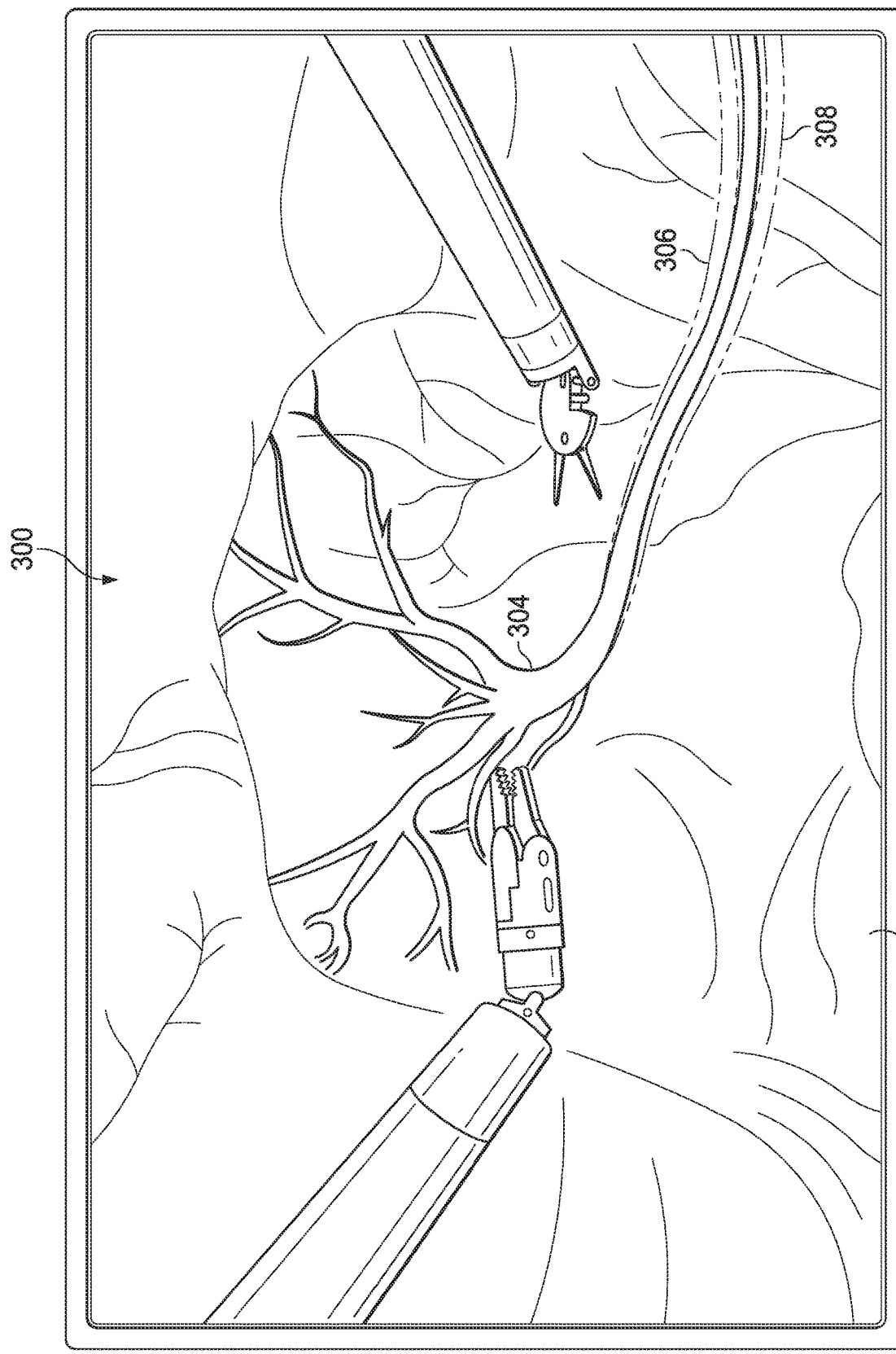
FIG. 6 is a display of a surgical environment image including an alert indication according to another example.

At a process 152, a surgical field of view image is displayed, for example on a display of the surgeon's console 16. The surgical field of view image may be a two or three dimensional image obtained by an endoscopic system (e.g., system 15, 28). At a process 154, an anatomic model image (e.g. from an external, non-invasive imaging system) is displayed on the same display with the field of view image, for example as an overlaid or superimposed image. Both the anatomic model image and the field of view image may be three dimensional. Together, the anatomic model image and the field of view image form the surgical environment image. The combined images allow the surgeon to visualize the surfaces of the surgical site surrounding the medical instruments but also allow visualization of internal structures not visible with the endoscopic image. FIG. 6 illustrates one example of a displayed surgical environment image 300 including an endoscopic field of view image 302 and an overlaid anatomic model image 304.

At a process 156, alert information from one or more components of the teleoperational system 10 is received. The alert information may be, for example, a warning, status information, error information, instructions from a mentor or proctor at another surgical console, or information about a next step in a surgical procedure. In this example, the alert information is error information regarding the registration of the patient anatomic model image 304 with the field of view image 302. An error in the registration may cause the surgeon to have a mistaken understanding of the spatial relationship between the surface anatomic structures visible in endoscopic image and the internal anatomic structures visible with the anatomic model images. Various registration techniques and methods for determining registration uncertainty have been described. For example, P.C.T. Application No. PCT/US2015/020891 (filed Mar. 17, 2015) (disclosing "Method and Devices for Tele-Surgical table Registration") which is incorporated by reference herein in its entirety, discloses relevant techniques. U.S. patent application Ser. No. 14/862,692 (filed Sep. 23, 2015) (disclosing "Collision Avoidance During Controlled Movement of Image Capturing Device and Manipulatable Device Movable Arms"), which is incorporated by reference herein its entirety, also discloses relevant techniques.

At a process 158, an alert indication is provided by modulating one of the field of view image or the anatomic model image relative to the other. As shown in FIG. 6, a registration error alert may be provided by modulating (e.g., providing animated vibration to) the anatomic model image 304 with respect to the field of view image 302. In this example, the model image 304 is modulated between an upper displacement limit 306 and a lower displacement limit 308. The magnitude of the animated vibration may correspond to the uncertainty in the registration. For example, if the uncertainty in the registration is +/−2 mm, the overlaid anatomic model image may be animated to modulate in one direction (e.g. up/down or right/left) by +/−2 mm.

In this example, the modulated image is the sub-portion of the surgical environment image 300 including the model image 304. More specifically, a three dimensional point cloud of image pixels forming the model image 304 (or a portion of the model image 304) in the surgical environment image 200 are identified. The point cloud is geometrically modulated (e.g., by moving some or all other points linearly in the image plane or in and out of the image plane of the stereoscopic image) to create an animated image of the model 304. For example, the animation may create the appearance that the image that the model 304 is vibrating, pulsating, or undulating in a wave form. Alternatively, the subportion of the image 300 including the model 304 may be altered by applying a blur or fade effect to the image of the model 304 to create the alert indication.

In various alternative examples, portions of the registered model image 304 and endoscopic image 302 may be modulated together to provide an alert indication about a region of activity. For example, a portion of the combined surgical environment image 300 may be modulated to indicate a region of activity or an instrument of interest. In various alternative examples, the alert indication can be used to provide instruction from a proctor or tele-mentor at another surgical console. For example, the alert indication may be used by the proctor to indicate that the surgeon should treat a specific tissue area shown in the field of view and/or anatomic model. In various alternative examples, the alert indication may be a local change in image parameters such as pixel brightness, color, or gray-scale. In various alternative examples, the alert indication may animate an anatomic tissue area shown in the field of view and/or anatomic model to show the surgeon a suggested next task or action in a surgical procedure. In various embodiments, the image of the instrument or tissue of interest in the alert indication may be held still while other portions of the surgical environment image are modulated.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method comprising:
   displaying a surgical environment image, the surgical environment image including a field of view image obtained by a first imaging system;
   receiving alert information; and
   providing an alert indication, based upon the alert information, within the surgical environment image by altering a portion of the surgical environment image, wherein altering the portion of the surgical environment image includes generating a cut-away view of anatomic tissue in the field of view image.

2. The method of claim 1, wherein altering the portion of the surgical environment image further includes animating movement of anatomic tissue being cut away in the generated cut-away view.

3. The method of claim 1, wherein the cut-away view provides an indication to a user to cut a portion of the anatomic tissue.

4. The method of claim 1, wherein the cut-away view provides an indication of a blood vessel to select for cauterization.

\* \* \* \* \*